United States Patent [19]
Leone et al.

[11] Patent Number: 5,902,266
[45] Date of Patent: May 11, 1999

[54] METHOD FOR DELIVERING A LIQUID SOLUTION TO THE INTERIOR WALL SURFACE OF A VESSEL

[75] Inventors: James E. Leone, Miami; Willard W. Hennemann, III, Davie; Stephen M. Rowland, Miami, all of Fla.

[73] Assignee: Cordis Corporation, Miami Lakes, Fla.

[21] Appl. No.: 09/087,873

[22] Filed: Jun. 1, 1998

Related U.S. Application Data

[62] Division of application No. 08/304,163, Sep. 12, 1994.

[51] Int. Cl.$^6$ .................................................. A61M 31/00
[52] U.S. Cl. .............................. 604/53; 604/52; 604/96; 606/108; 606/194
[58] Field of Search ..................... 604/8, 891.1, 890.1, 604/280, 281, 283, 264, 104, 96, 93, 49, 51, 52, 53, 265, 266; 606/191–198, 108; 128/898; 623/1, 11, 12, 66

[56] References Cited

U.S. PATENT DOCUMENTS

| | | |
|---|---|---|
| 4,681,570 | 7/1987 | Dalton . |
| 4,693,243 | 9/1987 | Buras ......................................... 604/96 |
| 4,878,906 | 11/1989 | Lindemann et al. . |
| 4,913,683 | 4/1990 | Gregory . |
| 5,019,090 | 5/1991 | Pinchuk . |
| 5,041,126 | 8/1991 | Gianturco . |
| 5,158,548 | 10/1992 | Lau et al. . |
| 5,234,456 | 8/1993 | Silvestrini . |
| 5,342,301 | 8/1994 | Saab . |
| 5,342,348 | 8/1994 | Kaplan . |
| 5,342,387 | 8/1994 | Summers . |
| 5,441,516 | 8/1995 | Wang et al. . |
| 5,443,495 | 8/1995 | Buscemi et al. . |
| 5,523,092 | 6/1996 | Hanson et al. . |
| 5,609,574 | 3/1997 | Kaplan et al. ............................ 604/53 |
| 5,716,410 | 2/1998 | Wang et al. . |

*Primary Examiner*—Ronald Stright
*Attorney, Agent, or Firm*—Thomas R. Vigil; Dean Garner

[57] ABSTRACT

The drug delivery stent assembly includes a hollow tubular wire stent which extends in a path defining a generally cylindrical envelope and which has side walls facing outwardly of the cylindrical envelope with holes therein for delivery of liquid to a site in a vessel where the stent is placed. The method for delivering a liquid solution to the interior wall surface of a vessel using the hollow tubular wire stent comprises: placing the stent on a balloon of a balloon on a wire guidewire or on a balloon catheter; inserting the stent on the balloon assembly at a desired site in a vessel; causing the balloon to expand the stent to a larger cylindrical shape; supplying liquid with a liquid supply source to the stent prior to or after placement of the stent so that liquid can be delivered from the outer holes in the stent to the site of placement of the stent in a vessel; disengaging the liquid supply source from the stent prior to or after placement of the stent in a vessel; and allowing the liquid solution to leak from the stent through the outwardly facing holes in the stent.

13 Claims, 3 Drawing Sheets

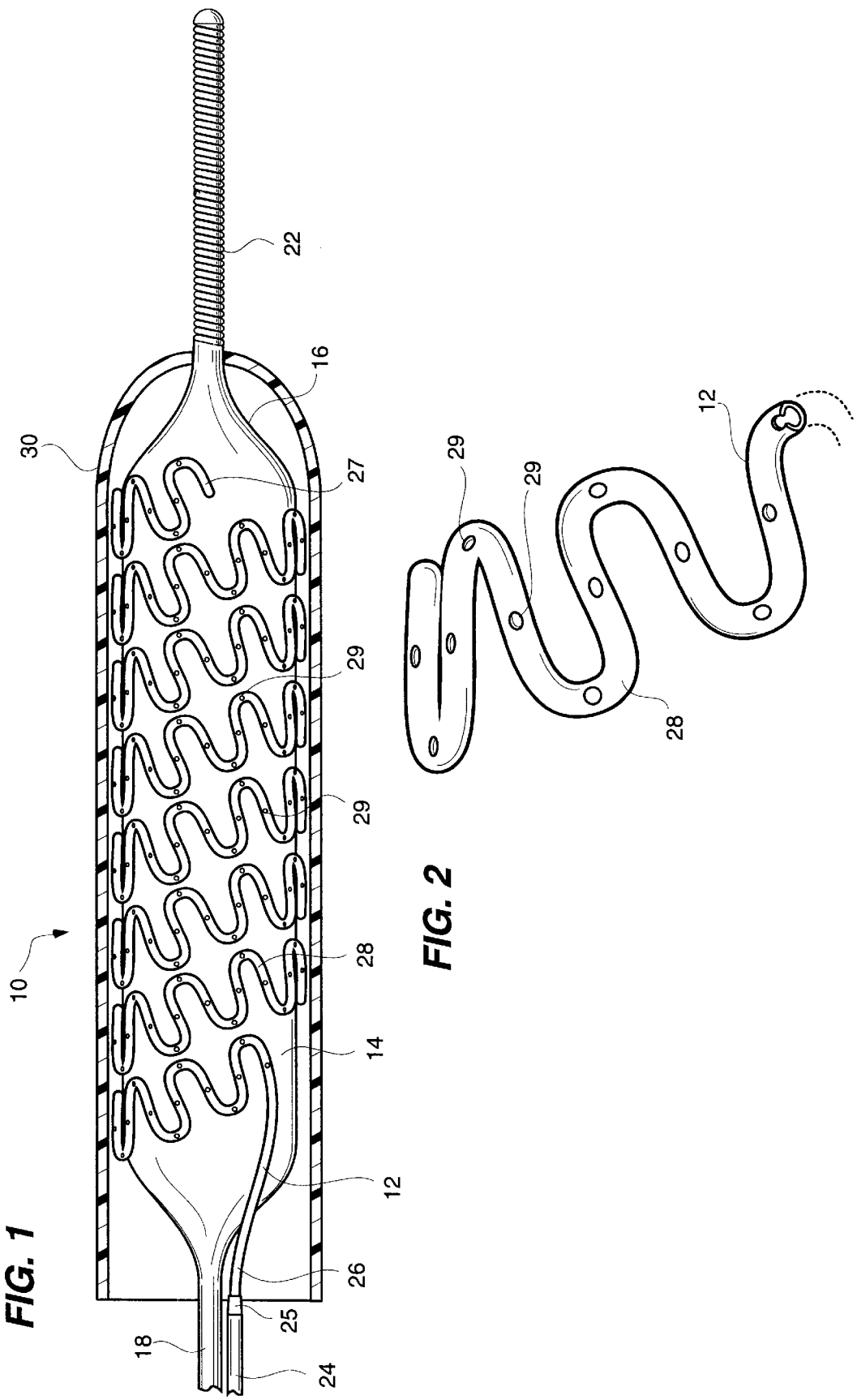

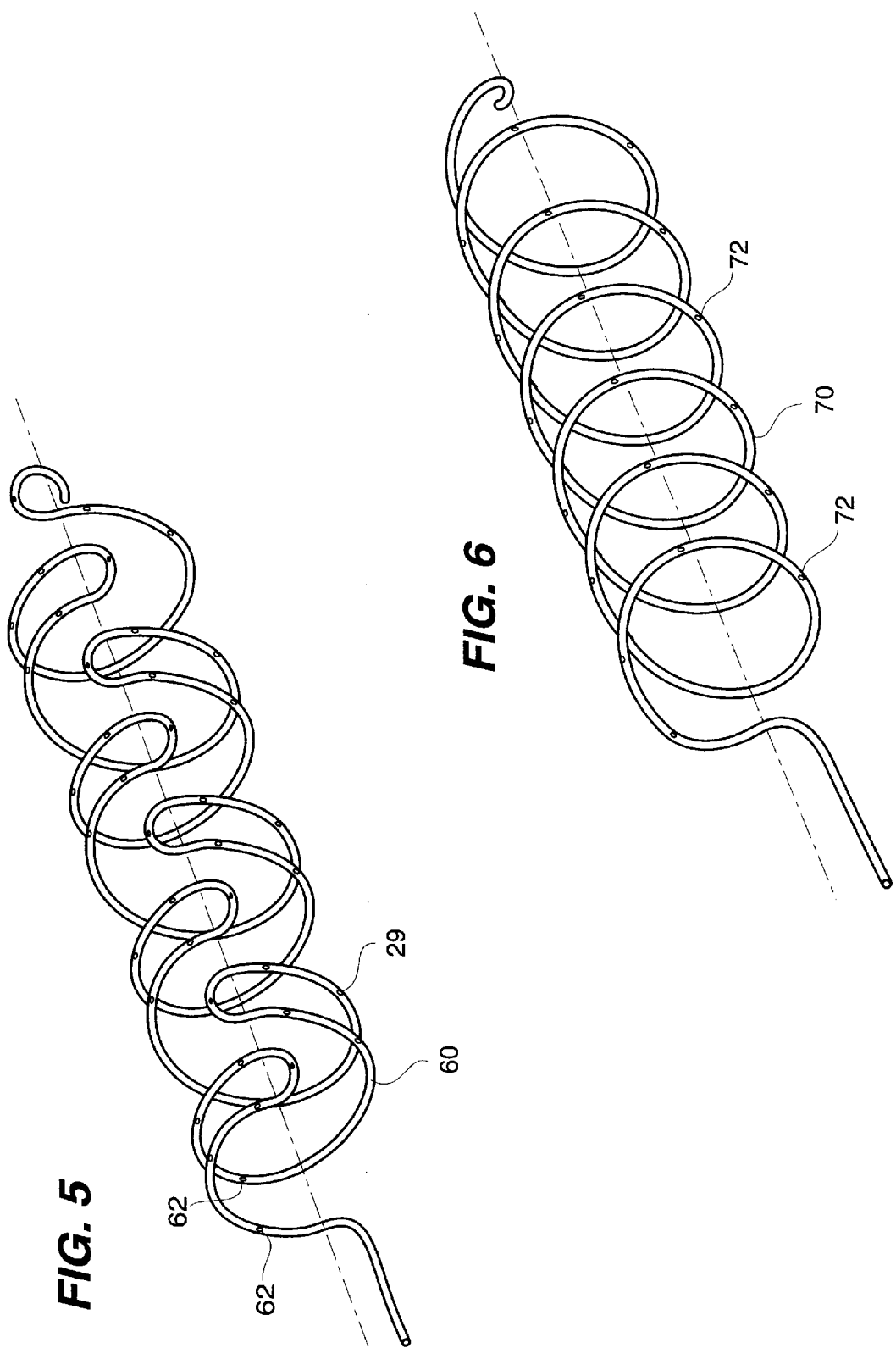

METHOD FOR DELIVERING A LIQUID SOLUTION TO THE INTERIOR WALL SURFACE OF A VESSEL

This is a division of application Ser. No. 08/304,163 filed on Sep. 12, 1994, now allowed.

BACKGROUND OF THE INVENTION

1. Field of the Invention

The present invention relates to a retrievable drug delivery stent which is made of a hollow tubular wire and which can be carried on a balloon of a balloon catheter to a site of a stenotic lesion where the stent is implanted. Subsequently, a balloon catheter can be inserted into the area of the stenotic lesion and a balloon can be positioned within the stent and by heating or cooling the stent with fluid supplied to the balloon, causing the stent to take another form, namely a retracted form. Then the stent and balloon can be removed. The hollow tubular wire stent is preferably made of a metal, such as stainless steel, tantalum or perhaps even from a nickel titanium alloy sold under the trademark Nitinol which can assume different shapes based upon the temperature of the Nitinol™. The tubing has holes therein for delivering a liquid solution or drug to a stenotic lesion. The hollow tubular wire stent also can be made of a plastic material.

2. Description of the Related Art Including Information Disclosed Under 37 C.F.R. 21211.97-1.99

Heretofore, wire stents have been proposed and one example of an undulating wire stent which extends in an undulating pattern back and forth in circular paths connected by loops to form a generally cylindrical envelope and which is adapted to be received on a balloon of a balloon catheter for insertion into a blood vessel to a site of a stenotic lesion is disclosed in the Gianturco U.S. Pat. No. 5,041,126.

Another example of a wire stent, preferably made of Nitinol™ that extends in an undulating manner in a helical path in a cylindrical envelope is disclosed in the Pinchuk U.S. Pat. No. 5,019,090.

A stent delivery system, which includes a sheath that is received about a balloon carrying a stent for facilitating insertion of the assembly of the sheath, stent, and balloon on a wire guidewire to a site of a stenotic lesion is disclosed in the Lau et al. U.S. Pat. No. 5,158,548.

Further, there has been disclosed in the Silverstrini U.S. Pat. No. 5,234,456, a hydrophilic stent which can be made of hollow tubular members. The hollow walls of the tubular members have hydrophilic material therein containing a drug and are fabricated of a semi-permeable material so that liquid can pass therethrough to swell the hydrophilic material.

As will be described in greater detail hereinafter, the hollow tubular stent of the present invention extends in a cylindrical envelope about a balloon and has holes therein that face outwardly of the cylindrical envelope whereby a drug can be delivered to the area of a stenotic lesion through the holes in the hollow wire tubular stent. After the stent is implanted at the site of the stenotic lesion and a fluid delivery tube is left in place connected to the stent for supplying liquid thereto, such as a liquid containing a drug, after a short period of time (a few days to a week or more), a dissolving fluid can be inserted into the liquid delivery tube for dissolving an end portion of the tube to disconnect the tube from the stent. Then, a balloon on a balloon catheter or a balloon on a wire guidewire can be reinserted into the vessel to the area of the stenotic lesion and partially inflated to assist in the withdrawal of the tubular wire stent from the area of the stenotic lesion.

The drug delivered to the area of the stenotic lesion can be of the type which dissolves plaque material forming the stenosis or can be an anti-platelet formation drug or an antithrombotic drug. Such drugs can include TPA, heparin, or urokinase, for example.

SUMMARY OF THE INVENTION

According to the invention, there is provided a drug delivery stent assembly including a wire stent made of a hollow tubular material which extends in a path defining a generally cylindrical envelope and which has side walls facing outwardly of the cylindrical envelope with holes therein for delivery of liquid to a site in a vessel where the stent is placed.

Further according to the invention, there is provided a method for delivering a liquid solution to the interior wall surface of a vessel using the stent described above and a balloon of a balloon on a wire guidewire or a balloon catheter, and includes the steps of: placing the stent on the balloon of a balloon on a wire guidewire or a balloon catheter; inserting the stent on the balloon assembly at a desired site in a vessel; causing the balloon to expand the stent to a larger cylindrical shape; supplying liquid with a liquid supply source to the stent prior to or after placement of the stent so that liquid can be delivered from the outer holes in the stent to the site of placement of the stent in a vessel; disengaging the liquid supply source from the stent prior to or after placement of the stent in a vessel; and, after the liquid solution has been allowed to leak from the stent through the outwardly facing holes in the stent, removing the stent from the vessel.

BRIEF DESCRIPTION OF THE DRAWINGS

FIG. 1 is a longitudinal view, partially in section and partially broken away, of a distal portion of a sheath, stent, balloon and balloon catheter assembly constructed according to the teachings of the present invention.

FIG. 2 is an enlarged portion of a helically and undulating extending hollow tubular wire stent which extends in a cylindrical envelope around the balloon shown in FIG. 1 and shows holes in the outwardly facing portions of the tubular wire stent in accordance with the teachings of the present invention.

FIG. 5 is a perspective view of another configuration for a hollow tubular wire stent which can be used in place of the undulating helically extending stent shown in FIGS. 1, 2 and 3.

FIG. 6 is a perspective view of another configuration for a hollow tubular wire stent, namely a coiled wire spring type configuration, which can be used in place of the stents shown in FIG'S. 1 and 5.

DESCRIPTION OF THE PREFERRED EMBODIMENT(S)

Figure 3:
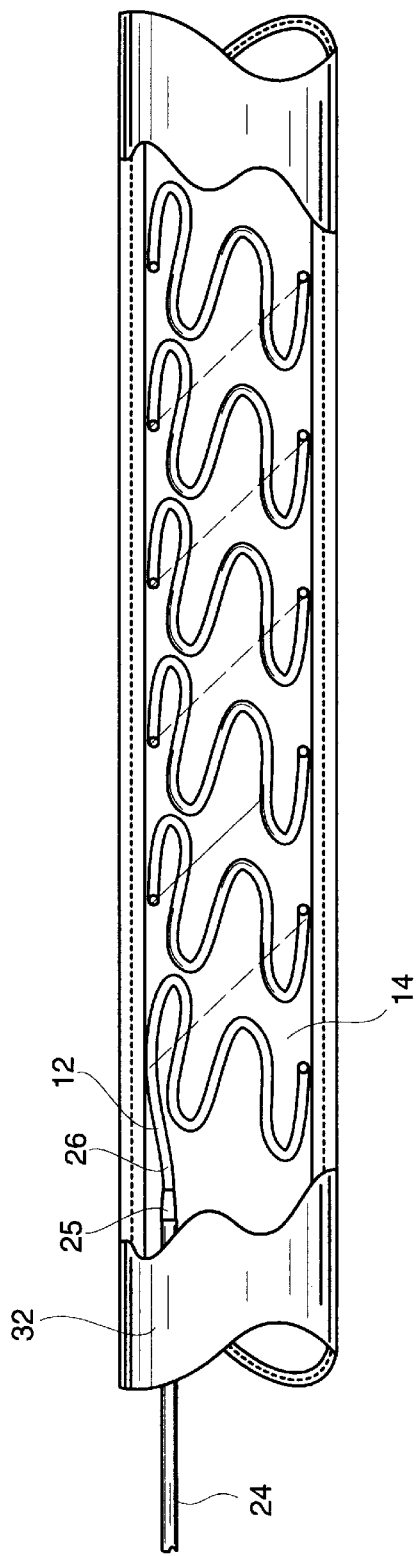
FIG. 3 is a longitudinal view, partially in section and with portions broken away, of a blood vessel within which the stent is implanted.

Referring now to the drawings in greater detail, there is illustrated in FIG. 1 a stent delivery system 10 constructed according to the teachings of the present invention and including a hollow metal tubular wire stent 12 which can made of stainless steel, tantalum or even from a formable material, such as a nickel titanium alloy sold under the trademark Nitinol and which extends in an undulating manner in a helical path around a balloon 14 of a balloon catheter 16 or a balloon on a wire (BOAW) guidewire 16. The BOAW guidewire 16 includes a catheter 18, the balloon 14 and, at its distal end, a highly flexible coiled spring wire tip 22. Proximal to the coiled spring wire tip 22 and mounted on the catheter 18 is the balloon 14. The remainder of the catheter 18 extends proximally to a steering mechanism and an infusion port (not shown) for steering the BOAW guidewire 16 to a site of a stenotic lesion and for enabling an inflating liquid to be supplied to the balloon 14.

According to the teachings of the present invention, mounted on the balloon 14 is the hollow metal tubular wire stent 12 which extends in an undulating manner in a helical path around the balloon 14 thereby defining a generally cylindrical envelope surrounding the balloon 14.

Also according to the teachings of the present invention, a liquid delivery tubing 24 has a distal end portion 25 fixed to a proximal end 26 of the hollow metal tubular wire stent 12. It will be understood that a distal end 27 of the stent 12 is closed. On the portions 28 of the hollow metal tubular stent 12 which are on the outside of the cylindrical envelope that the stent 12 defines, there are formed, such as with a laser beam, small ports or holes 29 in the tubular stent 12 whereby liquid can be dispensed from those holes 29 to the area of the stenotic lesion.

If desired and as shown, a sheath 30 can be provided surrounding the stent 12 on a balloon 14 shown in FIG. 1 to facilitate tracking of the sheath 30, stent 12, balloon 14 and balloon on wire a guidewire 16 through a blood vessel 32 (FIG. 3) to a site of a stenotic lesion.

The sheath 30 can be of the type disclosed in Lau et al. U.S. Pat. No. 5,453,090 entitled METHOD OF STENT DELIVERY THROUGH AN ELONGATE SOFTENABLE SHEATH.

FIG. 2 illustrates in larger detail the holes 29 that are formed in outer facing sides 28 of the hollow metal tubular stent 12.

FIG. 3 shows the stent in a blood vessel 32 after it has been positioned in the blood vessel 32 and the balloon on a wire guidewire 16 has been withdrawn and, if a sheath 30 was used, the sheath 30 also has been withdrawn.

Figure 4:
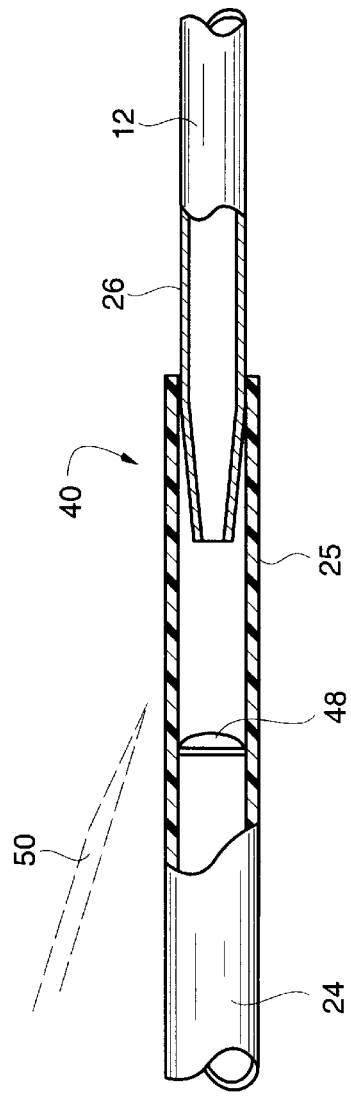
FIG. 4 is an enlarged view with portions broken away and partially in section of the connection of a proximal end of the tubular wire stent to the distal end of a liquid delivery tube and shows, in phantom, a hypodermic needle which can be inserted into a distal end portion of the liquid delivery tube for supplying liquid to the tubular wire stent.

FIG. 4 is an enlarged fragmentary view, partially in section, of a coupling arrangement 40 between the proximal end 26 of the hollow metal tubular stent 12 and the distal end portion 25 of the liquid/drug delivery tubing 24 connected to the proximal end 26 of the stent.

In one embodiment of the liquid/drug delivery tubing 24, a plug or seal 48 can be provided in the distal end portion 25 of the liquid/drug delivery tubing 24. Also if desired, just prior to the insertion of the stent 12 and balloon 14 into the blood vessel 32 or into a sheath 30 for introduction into the blood vessel 32, a hypodermic needle 50, shown in phantom, can be used to penetrate the distal end portion 25 of the liquid/drug delivery tubing 24 to insert a drug therein.

Also, of course, the plug 48 can be eliminated and is only an optional feature.

Once the stent 12 is implanted as shown in FIG. 3, a drug, such as a drug that is effective in dissolving plaque in a stenotic lesion, can be injected through the delivery tubing 24 to the hollow stent 12 and then out the holes 29 in the outer periphery of the stent 12 for treating the stenotic area.

Other drugs that can be delivered by the stent in a cardiovascular procedure can include an anti-platelet or platelet inhibiting drug such as Heparin or an anti-thrombotic drug such as Urokinase or possibly TPA. Also, the liquid supplied to the stent can be selected from the group consisting essentially of anti-proliferative agents, anti-sense agents, anti-bodies, anti-clotting agents and any other agents which serve to prevent stenosis in a blood vessel.

Of course the stent 12 with the holes 29 therein can be used for delivering other medications to the walls and interior of a body vessel.

In one embodiment, the stent 12 can have two states of size or shape, this being effected by using a Nitinol™ material which can have one shape or state at one temperature and can be caused to take another shape or state at another temperature. Heat can be supplied by a heated saline solution or by body heat.

After a sufficient treatment of the walls of the vessel at the site of placement, with a liquid or drug supplied to the hollow stent 12 vis-a-vis the liquid/drug delivery tubing 24, a liquid, such as a heated liquid or a body fluid compatible solvent, can be inserted into the liquid/drug delivery tubing 24, and particularly to the distal end portion 25 thereof to dissolve the connection of the drug delivery tubing 24 to the proximal end 26 of the hollow tubular stent 12 thereby to facilitate retrieval of the drug delivery tubing 24.

At the same time or afterwards, a balloon 14 such as a balloon on a wire guidewire or a balloon 14 on a balloon catheter 16, can be inserted into the vessel to place the balloon 14 in the area of the stent 12 and the balloon 14 is then inflated to come into contact with the stent 12. Then a liquid having a temperature which will cause a change in state of the hollow metal tubular stent 12 is injected into the balloon 14. For example, a saline solution at room temperature can be circulated in a partially expanded balloon 14 adjacent the stent 12 to cause the stent to contract to its smaller shape whereupon the balloon 14 can be inflated slightly to engage the stent 12 and then the balloon catheter or balloon on a wire guidewire 16 can be withdrawn to remove the stent 12 from the vessel.

Another type of stent 60 which is similar to the type of stent disclosed in U.S. Pat. No. 5,041,126 is illustrated in FIG. 5. It is to be understood, of course, that other shapes of hollow tubular stents 12 can be utilized and the material from which the hollow tubular stent is made can be metal or non-metal, i.e., it can be made out of a polymer material.

If desired, additional holes 62 can be provided in the walls of the stent 60 (or of the other stents disclosed herein) that open into lumen of the blood vessel as shown in FIG. 5. Such holes 62 would typically be located at a distal end or proximal end of the stent, preferably at the upstream end of the stent relative to the liquid flow through the vessel.

The stent can have a coiled spring shape, i.e., such as the stent 70 shown in FIG. 6 having holes 72 in an outer wall thereof, as opposed to the shape of the stent 12 and the shape of the stent 60.

Typically the hollow tubing from which the stent 12, 60 or 70 is made has an outer diameter of 0.008 inches ±0.002 inches and an inner diameter of 0.005 inches ±0.002.

The stent must have a length which enables it to be balloon deployable, i.e. 1.5 centimeters for a 2 centimeter length balloon. A coiled spring type stent 70 will then have a length of 8–12 inches when uncoiled.

Furthermore, the stent, e.g. the stent 12, the stent 60 or the stent 70 can be a permanently implanted stent. As shown in FIG. 6, the stent 70 can be a coiled stent made out of a material such as stainless steel or tantalum which does not change shapes with temperature changes, but which can be retrieved into a sheath, such as the sheath 30, by utilizing the liquid delivery tubing 24 as a tether. In this respect, the sheath 30 can be moved adjacent to the stenotic site and the coiled stent 70 can then be pulled into the sheath 30.

It will be understood that as a coiled spring type stent 70 sheath is pulled, it stretches slightly and contracts in diameter slightly such that during pulling it has a smaller outer diameter than when implanted to facilitate its removal.

Also a partially inflated balloon of a balloon catheter can be inserted into and within the envelope of the coiled stent 70 before, as it is being pulled into, or after it is pulled into, the sheath 30 followed by inflating the balloon to the inner diameter of the stretched coiled spring stent so that the balloon catheter can be used to assist in withdrawing the stent from the blood vessel.

From the foregoing description it will be understood that the retrievable drug delivery stent 12, 60 or 70 of the present invention has the advantage of the use of a temporarily implanted hollow tubular stent 12, 60 or 70 that serves not only as a stent 12, but also as a delivery system for delivery of a drug solution vis-a-vis the holes or pores 29 (and holes 62 or 72 if provided) that are laser drilled into the stent 12, 60 or 70. Preferably the stent 12, 60 or 70 is made of Nitinol™. Contraction or expansion of the stent 12 is facilitated by utilizing the shape memory of Nitinol™ to cause the stent 12 to collapse back onto a retrievable balloon catheter upon exposure to temperatures in excess of 50° C. as with the ACT Eigler-Litvack HARTS device.

However the stent 12, 60 or 70 can be manufactured of any material including stainless steel or tantalum so long as the stent 12, 60 or 70 is retrievable. The hollow nature of the stent 12, 60 or 70 allows the stent 12, 60 or 70 to be loaded at the time of implantation with a solution of whatever drug the user wishes delivered. The solution then is delivered via the pores or holes 29 drilled at substantially equidistantly spaced intervals over the outer surface of the stent 12, 60 or 70. The pores or holes 29 are the size that is small enough to prevent rapid leakage, but large enough to allow slow leakage of solution over a period of several days to a week.

Also from the foregoing description, it will be apparent that modifications can be made to the retrievable drug delivery stent 12, 60 or 70 of the present invention without departing from the teachings of the invention. Accordingly, the scope of the invention is only to be limited as necessitated by the accompanying claims.

We claim:

1. A method for delivering a liquid solution to the interior wall surface of a blood vessel comprising:

providing a hollow tubular wire stent which extends in a path defining a generally cylindrical envelope and which has side walls facing outwardly of the cylindrical envelope with holes therein for delivery of liquid to a site of placement in a blood vessel where the stent is placed on a balloon of a balloon on a wire guidewire or a balloon catheter;

placing the stent on a balloon of a balloon on a wire guidewire or a balloon catheter;

inserting the stent on said balloon to a desired site in a blood vessel;

causing the balloon to expand the stent to a larger cylindrical shape; and, supplying liquid with a liquid supply means to the stent prior to or after inserting the stent so that liquid can be delivered from the outer holes in the stent to the site of the stent in the blood vessel.

2. The method of claim 1 wherein said stent is a coiled spring type stent and said liquid supply means is a liquid delivery tubing coupled to a proximal end of the stent, said method further including the steps of: using the liquid delivery tubing as a tether; pulling the liquid delivery tubing to stretch the coiled spring stent thereby reducing its diameter and loosening it from its place of implantation; and, withdrawing the stent from the blood vessel.

3. The method of claim 2 including the step of placing a sheath in the blood vessel adjacent the location of the implanted stent followed by the steps of pushing the stent into the sheath.

4. The method of claim 3 including the step of inserting a partially inflated balloon in the sheath near the distal end thereof and placing the partially inflated balloon in the cylindrical envelope of the stent before, as it is being pushed, or after it is pushed into the sheath; inflating the balloon to the inner diameter of the stretched coiled spring stent; and, withdrawing the stent balloon and sheath from the blood vessel.

5. The method of claim 1 wherein the liquid supply means includes a liquid delivery tubing and a proximal end of the stent is coupled to a distal end portion of the liquid delivery tubing and said liquid supplying step includes supplying liquid to the stent prior to the insertion of the stent into the blood vessel.

6. The method of claim 5 wherein said supplying of liquid is effected with a hypodermic needle which is injected into the distal end portion of the liquid delivery tubing.

7. The method of claim 1 including the step of disengaging the liquid supply means from the stent prior to or after inserting the stent in the blood vessel.

8. The method of claim 1 wherein liquid solution is supplied to the stent after insertion of the stent in the blood vessel through the liquid delivery tubing and said method includes the further step of, after a sufficient amount of liquid has been supplied through the drug delivery tubing, supplying a heated liquid or a human body compatible solvent to the distal end portion of the liquid delivery tubing to dissolve same whereby the liquid delivery tubing can be safely removed from the blood vessel.

9. The method of claim 1 including the further steps of after the liquid solution has been allowed to be delivered from the stent through the outwardly facing holes in the stent, removing the stent from the blood vessel.

10. The method of claim 1 wherein said liquid supplied to the stent includes a plaque dissolving liquid.

11. The method of claim 1 wherein the liquid supplied to the stent includes an anti-platelet forming or platelet inhibiting liquid.

12. The method of claim 1 wherein the liquid supplied to the stent includes an anti-thrombotic drug.

13. The method of claim 1 wherein the liquid supplied to the stent is selected from the group consisting essentially of anti-proliferative agents, anti-thrombotic agents, anti-sense agents, anti-bodies, anti-clotting agents and any other agents which serve to prevent stenosis in a blood vessel.

* * * * *